United States Patent
Allum et al.

(10) Patent No.: US 12,296,100 B2
(45) Date of Patent: *May 13, 2025

(54) CONFORMING NASAL PILLOW

(71) Applicant: INOGEN, INC., Goleta, CA (US)

(72) Inventors: Todd Allum, Livermore, CA (US); Eric Johansson, Dublin, CA (US)

(73) Assignee: Inogen, Inc., Goleta, CA (US)

( * ) Notice: Subject to any disclaimer, the term of this patent is extended or adjusted under 35 U.S.C. 154(b) by 168 days.

This patent is subject to a terminal disclaimer.

(21) Appl. No.: 18/174,263

(22) Filed: Feb. 24, 2023

(65) Prior Publication Data

US 2023/0211105 A1 Jul. 6, 2023

Related U.S. Application Data

(63) Continuation of application No. 15/327,371, filed as application No. PCT/US2015/041023 on Jul. 17, 2015, now Pat. No. 11,607,517.

(60) Provisional application No. 62/026,555, filed on Jul. 18, 2014.

(51) Int. Cl.
*A61M 16/06* (2006.01)
*A61M 16/08* (2006.01)
*A61M 16/12* (2006.01)

(52) U.S. Cl.
CPC .... *A61M 16/0672* (2014.02); *A61M 16/0666* (2013.01); *A61M 16/0816* (2013.01); *A61M 16/127* (2014.02)

(58) Field of Classification Search
CPC .......... A61M 16/0666; A61M 16/0672; A61M 16/0677; A61H 34/04; A61F 5/08; A62B 23/06
See application file for complete search history.

(56) References Cited

U.S. PATENT DOCUMENTS

| 8,042,539 | B2 | 10/2011 | Chandran et al. |
| 8,666,085 | B2 | 3/2014 | Donaldson et al. |
| 2003/0094178 | A1 | 5/2003 | McAuley |
| 2004/0103899 | A1 | 6/2004 | Noble |
| 2004/0226566 | A1 | 11/2004 | Gunaratnam |
| 2006/0174889 | A1 | 8/2006 | Noble |

(Continued)

FOREIGN PATENT DOCUMENTS

| WO | WO 2011/022779 A1 | 3/2011 |
| WO | WO 2013/168134 A1 | 11/2013 |
| WO | WO 2014042862 A1 | 3/2014 |

OTHER PUBLICATIONS

International Search Report for International Patent Application No. PCT/US2015/041023 dated Jan. 14, 2016.

*Primary Examiner* — Margaret M Luarca
(74) *Attorney, Agent, or Firm* — Knobbe, Martens, Olson & Bear, LLP (57) ABSTRACT

Embodiments of the present disclosure include a nasal pillow apparatus having a first nasal pillow, a second nasal pillow, and a connecting bar that connects the first nasal pillow to the second nasal pillow, the connecting bar being disposed below a bottom surface of the first nasal pillow and a bottom surface of the second nasal pillow. Each of the first nasal pillow and the second nasal pillow includes an inner wall having a first end and a second end opposite the first end; and an outer wall connected to the second end of the inner wall. When inserted into a nostril of a patient, the outer wall is configured to conform to the nostril by compressing in a first direction and expanding in a second direction.

20 Claims, 5 Drawing Sheets (56) References Cited

U.S. PATENT DOCUMENTS

| | | |
|---|---|---|
| 2006/0237017 A1 | 10/2006 | Davidson |
| 2007/0272249 A1 | 1/2007 | Chandran |
| 2008/0121230 A1 | 5/2008 | Cortez |
| 2009/0044808 A1 | 2/2009 | Guney |
| 2011/0214676 A1 | 9/2011 | Allum |
| 2012/0145158 A1 | 6/2012 | Lubke et al. |
| 2013/0081639 A1 | 4/2013 | Borjegren et al. |
| 2015/0250973 A1 | 9/2015 | Allum |
| 2016/0051784 A1 | 2/2016 | Eury |

CONFORMING NASAL PILLOW

CROSS-REFERENCE TO RELATED APPLICATIONS

This application is a continuation of U.S. patent application Ser. No. 15/327,371, filed on Jan. 18, 2017, which is a U.S. National Phase of PCT International Application No. PCT/US2015/041023, filed Jul. 17, 2015, which claims the benefit of U.S. Provisional Patent Application No. 62/026, 555, filed on Jul. 18, 2014. The subject matter of each of these related applications is hereby incorporated herein by reference.

BACKGROUND OF THE INVENTION

Field of the Invention

Embodiments of the present disclosure relate generally to ventilation systems, and more particularly to a conforming nasal pillow.

Description of the Related Art

A variety of ventilation systems have been developed to aid a patent who is physically unable to breathe or who needs breathing assistance. Traditional ventilation systems include continuous positive airway pressure (CPAP) systems, bilevel positive airway pressure (BiPAP) systems, volume support/control systems, and pressure support/control systems. Such ventilation systems utilize large-diameter breathing tubes, also referred to herein as large-bore breathing tubes connected to a non-invasive mask worn by the patient. The diameter of these large-bore breathing tubes is typically in the range of 15 mm to 22 mm. With these ventilation systems, substantially all of the patient's inhaled gas is delivered through the large-bore breathing tube. The exhaled gas exits through either an expiratory limb, in the case of dual lumen circuits, or via an array of holes in the mask, in the case of a single lumen circuit. A ventilator-induced flow, referred to herein as a "bias flow," is commonly maintained through the tubing during the exhalation phase in order to keep the breathing tubes and mask free of elevated carbon dioxide levels due to exhalation by the patient.

Traditional non-invasive masks have a relatively large size in order to physically accommodate the attachment of a large-bore tube, such as 15 mm or 22 mm, provide enough flow area for the bias flow, and allow for adequate exhalation area. The infrastructure required to support these features adds unwanted volume in the exhalation circuit or mask. This unwanted volume, referred to herein as "dead space," is the space within the mask in which the breathing gas flows in both directions as the patient inhales and exhales. Typically, the dead space needs to be flushed of excess carbon dioxide during each exhalation cycle.

Further, some ventilation masks are fitted with nasal pillows, also referred to herein as nasal cushions, for non-invasive nasal ventilation directly into the nares, or nostrils, of the patient. Such nasal pillows generally consist of a concave conical distal surface that interfaces with and seals with the nasal openings of the patient. This concave surface allows for insertion into various nasal opening sizes. The sealing area of such nasal pillows is around the outer edge of the nasal opening or around the outer edge of the nose surface surrounding the nasal openings when compressed with headgear. At the base of the concave surface, that is, at the bottom half of the pillow, the nasal pillow has the form of a mushroom shape that allows the pillow, when worn under compression, to press against the nostril openings of the patient, thereby forming an adequate seal.

One drawback with these traditional non-invasive ventilation masks is that the physical volume needed to accommodate large-bore breathing tubes results in a relatively large mask design. However, large ventilation masks are often clumsy and difficult to maneuver when placing onto and removing from the patient. In addition, larger masks are often uncomfortable to wear, relative to smaller masks. Another drawback with such ventilation masks is that energy absorbing devices, head straps, or other headgear are typically required to form a compression seal around the patient's nostrils and to prevent the mask and associated nasal pillows from being dislodged. Such devices and headgear typically results in further discomfort to the patient.

As the foregoing illustrates, there is a need for more effective pillow design that is more conforming to a wider range of nasal shapes and sizes than conventional designs.

SUMMARY OF THE INVENTION

Embodiments of the present disclosure include a nasal pillow with an inner wall having a first end and a second end opposite the first end. The nasal pillow further includes an outer wall connected to the second end of the inner wall. When inserted into a nostril of a patient, the outer wall is configured to conform to the nostril by compressing in a first direction and expanding in a second direction.

Embodiments of the present disclosure further include a nasal pillow apparatus having a first nasal pillow, a second nasal pillow, and a connecting bar that connects the first nasal pillow to the second nasal pillow, the connecting bar being disposed below a bottom surface of the first nasal pillow and a bottom surface of the second nasal pillow. In some embodiments, each of the first nasal pillow and the second nasal pillow may include an inner wall having a first end and a second end opposite the first end; and an outer wall connected to the second end of the inner wall. When inserted into a nostril of a patient, the outer wall may be configured to conform to the nostril by compressing in a first direction and expanding in a second direction.

At least one advantage of the disclosed techniques is that the size of an air entrainment mask and the associated nasal pillows is reduced relative to prior approaches. As a result, the breathing support device is less cumbersome for the patient to use.

BRIEF DESCRIPTION OF THE DRAWINGS

So that the manner in which the above recited features of embodiments of the invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

A nasal pillow design for delivering breathable gas, such as oxygen-enriched air, to a patient is presented in this disclosure. The disclosed nasal pillows include geometrical features to allow for insertion of the nasal pillows into the nares, provide sealing for positive pressure delivery, and allow anchoring of the interface without the need for retaining head straps.

Figure 1:
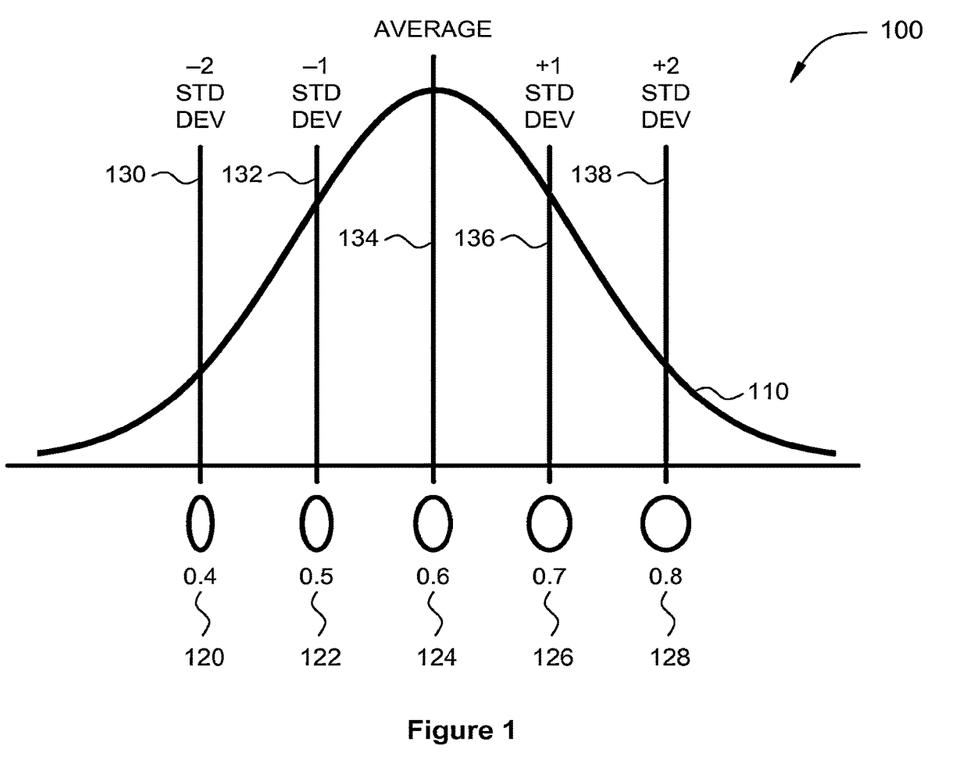
FIG. 1 illustrates an exemplary distribution of nasal profiles, according to one embodiment of the present invention.

FIG. 1 illustrates an exemplary distribution 100 of nasal profiles, according to one embodiment of the present invention. As shown, the exemplary distribution 100 takes the form of a normal curve 110. A generalization of the shape of the nasal opening is that of an ellipse. One significant variance in nasal shapes, from user to user, is the elliptical ratio, where the elliptical ratio is the width of the nasal opening, that is, in a direction substantially perpendicular to the septum, divided by the length of the nasal opening, that is, in a direction substantially parallel to the septum.

As shown in FIG. 1, the average 134, or mean, of the normal curve 110 corresponds to a nasal profile 124 with an elliptical ratio of 0.6. Nasal profiles with a smaller elliptical ratio than the average 134 include nasal profile 122 at −1 standard deviation (STD DEV) 132 with an elliptical ratio of 0.5, and nasal profile 120 at −2 standard deviations 130 with an elliptical ratio of 0.4. These nasal profiles represent individuals who have noses with narrow and elongated nares relative to the average naris. Nasal profiles with a larger elliptical ratio than the average 134 include nasal profile 126 at +1 standard deviation 136 with an elliptical ratio of 0.7 and nasal profile 128 at +2 standard deviations 138 with an elliptical ratio of 0.8. These nasal profiles represent individuals who have noses with nares that are more round in shape relative to the average naris.

Figure 2:
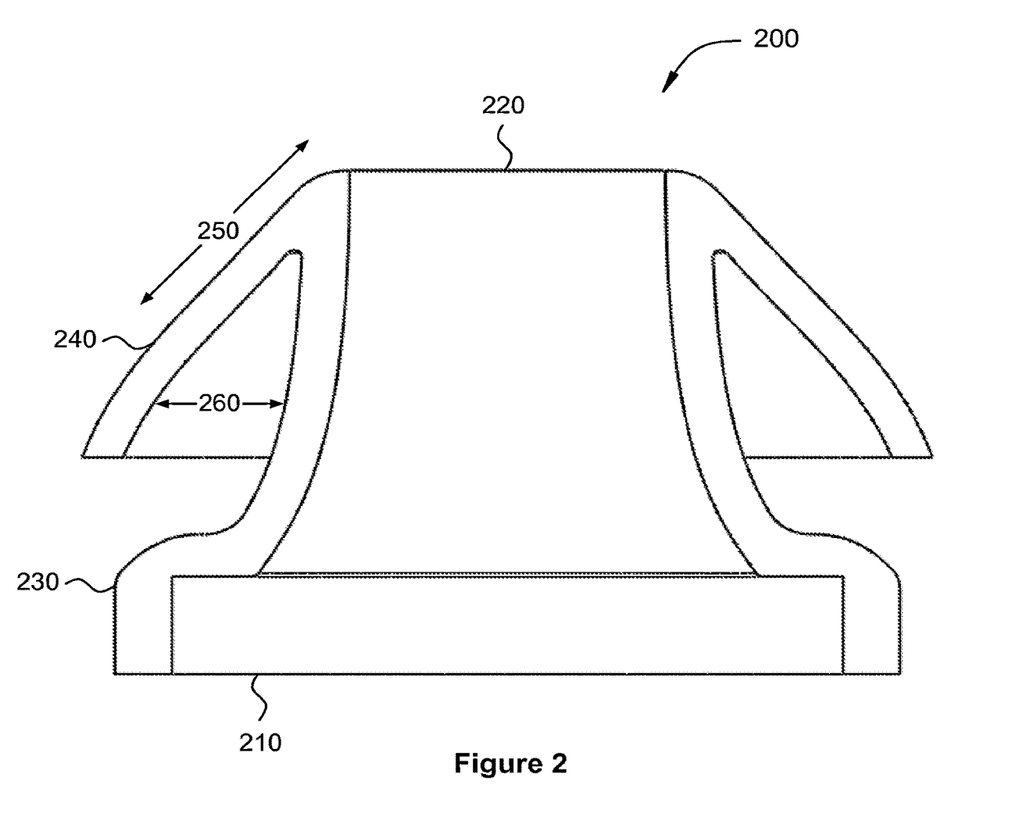
FIG. 2 illustrates a cross-sectional view of a nasal pillow, according to one embodiment of the present invention.

FIG. 2 illustrates a cross-sectional view of a nasal pillow 200, according to one embodiment of the present invention. As shown, the nasal pillow 200 includes, without limitation, an interconnection 210, an intermix cavity 220, an inner wall 230, and an outer wall 240.

The interconnection 210 connects the nasal pillow 200 to other components, such as an entrainment device (not explicitly shown), of the ventilation system. In general, an air entrainment device intermixes delivered oxygen with ambient air to deliver oxygen-enriched air and amplify the delivered flow, proximal to the patient. These types of entrainment devices reduce the flow requirements through the delivery tubes due to the flow amplification ratio that occurs near the patient, where the flow amplification ratio is typically greater than 3:1. In addition, entrainment devices negate the need for an expiratory limb, bias flow, or an array of exhalation holes, to aid in removing carbon dioxide resulting from exhalation. Rather, entrainment devices allow the patient to exhale directly to the ambient airspace without passing through any dead space. The air entrainment device connects directly to the nasal pillow 200 via the interconnection 210. In one embodiment, the interconnection 210 may include a counter bore, whereby a delivery tube of the air entrainment device is fastened to the interconnection 210 via an adhesive. In another embodiment, the interconnection 210 may be accomplished by over-molding the nasal pillow over an element of the air entrainment device. The amplification of delivered gas at the interface (resulting from entrainment of ambient gas) and the elimination of an expiratory limb significantly reduce the tubing size requirement leading to the mask. Rather than a large-bore tube of 15-22 mm in diameter, tubing having a diameter of less than 2 mm may be used with the disclosed nasal pillow. The elimination of an expiratory limb, bias flow requirements, and exhalation hole array, along with the reduction in required tube size, reduces or eliminates the need for large mask designs or infrastructure near the patient.

The intermix cavity 220 transmits oxygen-enriched air from the interconnection 210 to the distal, or top, end of the nasal pillow 200 when the patient inhales. Correspondingly, the intermix cavity 220 transmits carbon dioxide and other exhalation gases from the distal end of the nasal pillow 200 to the interconnection 210. The converging shape of the intermix cavity 220 is designed to increase efficiency of the entrainment device. By varying the amount of convergence in the shape of the intermix cavity 220, the entrainment ratio, or mix of oxygen to ambient area, is increased or decreased. In operation, the intermix cavity 220 effectively serves as a jet pump, where the concentration of oxygen within the intermix cavity 220 decreases as the efficiency of the intermix cavity 220 increases. The opening at the distal end of the intermix cavity 220 is sized to provide patient with enough space to inhale and exhale without significant resistance.

The inner wall 230 surrounds the intermix cavity 220 and provides the structure to physically support the entrainment device within the nostrils of the patient. The lower end of the inner wall is proximal to the interconnection 210. The inner wall 230 is relatively rigid, due to the geometric properties of the inner wall 230, which maintains the general shape of the intermix cavity 220, thereby providing relatively constant flow amplification performance for the entrainment device. The relative rigidity of the inner wall 230 allows the nasal pillow 200 to gimbal to accommodate various nostril angles without causing the intermix cavity 220 to collapse.

The outer wall 240 attaches to the inner wall 230 near the upper end of the nasal pillow 200. The outer wall 240 provides a conforming seal and anchoring mechanism within the patient's nose. The outer wall 240 forms a seal between the top end of the nasal pillow 200 and the inside of the patient's nostril. The radial stiffness of the outer wall 240 reduces as the distance from the attachment point to the inner wall 230 increases. This reduction in radial stiffness results from the increasing cantilevered length 250 of the outer wall and the increased radial gap 260 between the inner wall 230 and the outer wall 240. Further, The radial gap 260 between the inner wall 230 and the outer wall 240 is designed to accommodate a broad range of nasal profiles with varying elliptical ratios when inserted into the nose. Because of the relatively low radial stiffness of the outer wall 240, the nasal pillow 200 may be compressed during insertion. As a result, the nasal pillow 200 can be fully inserted into and retained by the nose with relatively low effort and without the need for head straps. The outer wall 240 expands after insertion into the nose, conforming to the nose over a wide range of elliptical ratios.

Figure 3A:
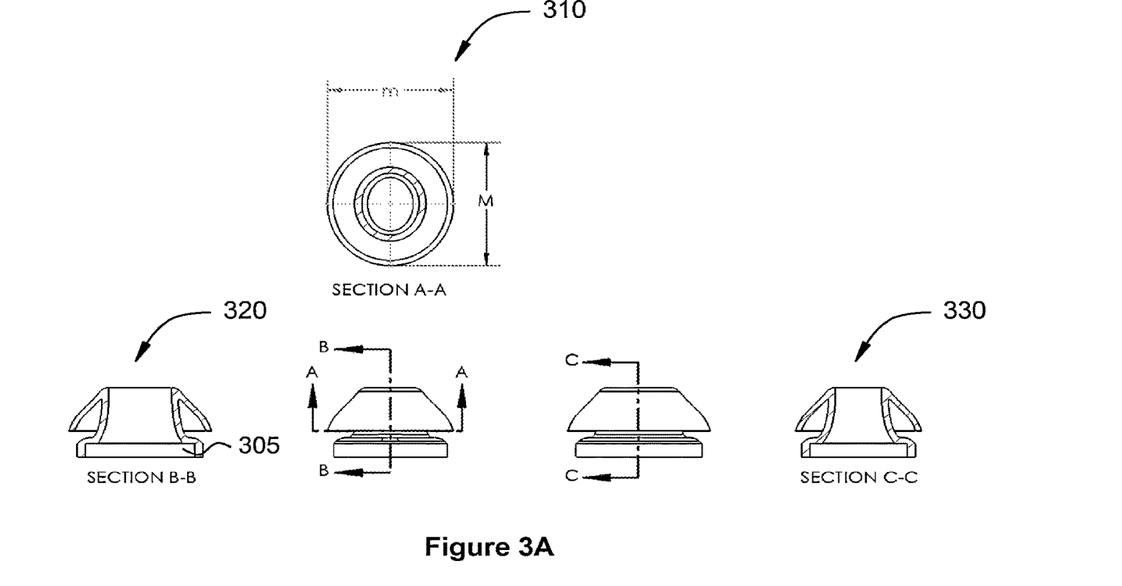
FIG. 3A illustrates various sectional views of the nasal pillow of FIG. 2, according to one embodiment of the present invention.

FIG. 3A illustrates various sectional views of the nasal pillow 200 of FIG. 2, according to one embodiment of the present invention. In the embodiments of FIG. 3A, the nasal pillow includes a counter bore 305, whereby a delivery tube of the air entrainment device is fastened to the nasal pillow 200 via an adhesive.

As shown in FIG. 3A, sectional view 310 illustrates an axial view at section A-A. As shown, the vertical dimension "M" of sectional view 310 is longer than the horizontal dimension "m" of sectional view 310. The vertical dimension "M" and the horizontal dimension "m" are also referred to herein as the major elliptical axis and the minor elliptical axis, respectively. Sectional view 320 illustrates a longitudinal view at section B-B along the major elliptical axis. That is, the width of the nasal pillow in sectional view 320 is "M." Correspondingly, sectional view 330 illustrates a longitudinal view at section C-C along the minor elliptical axis. That is, the width of the nasal pillow in sectional view 330 is "m." In some embodiments, the elliptical ratio of nasal pillow 200 may be given as m/M. As further described herein, the radial gap 260 between the outer wall 240 and inner wall 230 of the nasal pillow 200 is designed to accommodate a broad range of nasal profiles with various elliptical ratios when inserted into the nose. The geometry of the outer wall 240 of the nasal pillow 200 in the undeformed state is designed to accommodate a relatively large elliptical ratios as shown in FIG. 3A. In one example, the elliptical ratio m/M of the cross section of the outer wall 240 could be in the range of 0.8 to 1 prior to insertion into the naris of the patient.

Figure 3B:
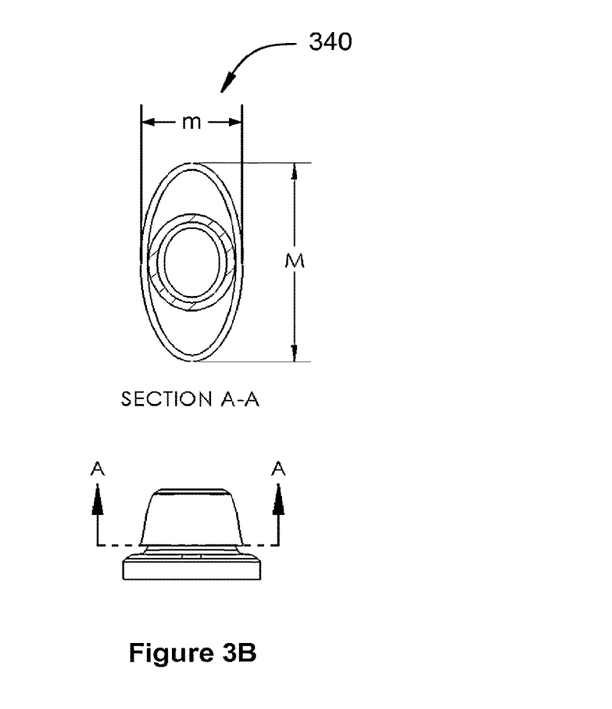
FIG. 3B illustrates the nasal pillow of FIG. 3A, in a deformed state as if inserted into a naris of a particular shape, according to one embodiment of the present invention.

FIG. 3B illustrates the nasal pillow of FIG. 3A, in a deformed state as if inserted into a naris of a particular shape, according to one embodiment of the present invention. As shown in FIG. 3B, the cross-sectional view 340 illustrates an axial view at section A-A after insertion into the nose of a patient. Due to the flexibility and allowable radial travel of the outer wall 240, the nostril pillow 200 may be inserted into nares that have a smaller elliptical ratio, such as m/M=0.4, with relative ease. During insertion into the naris, the nostril pillow 200 conforms to the naris by compressing in a first direction and expanding in a second direction. More specifically, during insertion, the nasal pillow is compressed in the direction of the minor elliptical axis, causing a corresponding elongation in the direction of the major elliptical axis. The nasal pillow reduces in length along the minor elliptical axes, resulting in an increase in length along the major elliptical axis. Stated another way, after insertion, the distance "m," in a direction substantially perpendicular to the septum, is less than the distance "m" prior to insertion. Correspondingly, the distance "M," in a direction substantially parallel to the septum, is greater than the distance "M" prior to insertion. In one example, the elliptical ratio m/M of the cross section of the outer wall 240 could be less than 0.8 after insertion into the naris of the patient. In another example, the elliptical ratio m/M of the cross section of the outer wall 240 could be in the range of 0.4 to 0.7 after insertion into the naris of the patient.

Figure 4:
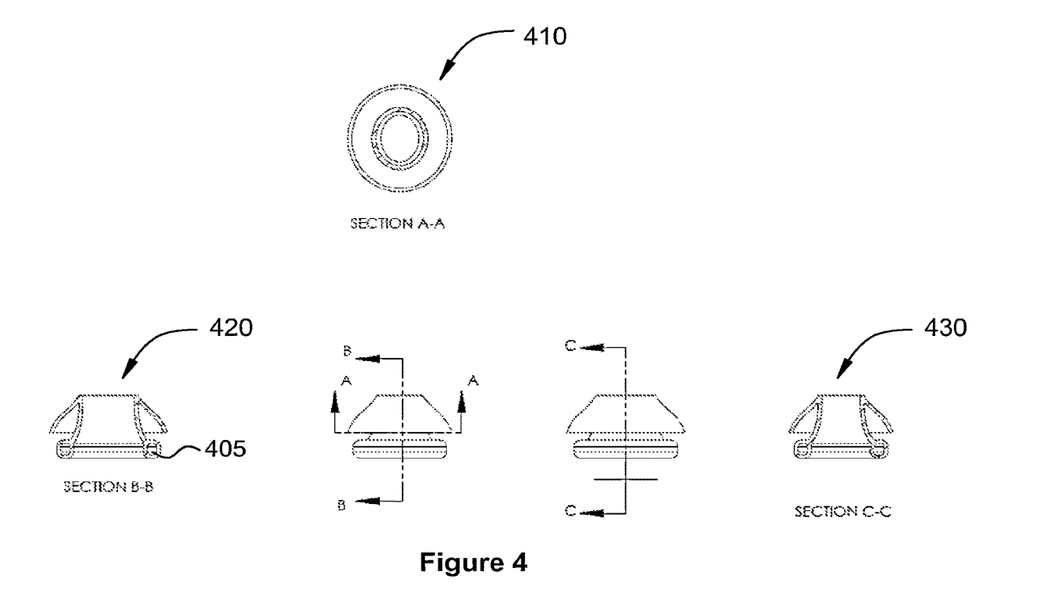
FIG. 4 illustrates various sectional views of a nasal pillow, according to another embodiment of the present invention.

FIG. 4 illustrates various sectional views of a nasal pillow, according to another embodiment of the present invention. Sectional view 410 illustrates an axial view at section A-A. Sectional view 420 illustrates a longitudinal view at section B-B along the major elliptical axis. Sectional view 430 illustrates a longitudinal view at section C-C along the minor elliptical axis. As shown in FIG. 4, the air entrainment device (not explicitly shown) is captured by the nasal pillow 420 via the interconnection 405. In one embodiment, the interconnection 405 may be accomplished by over-molding the nasal pillow 420 over an element of the air entrainment device.

Figure 5:
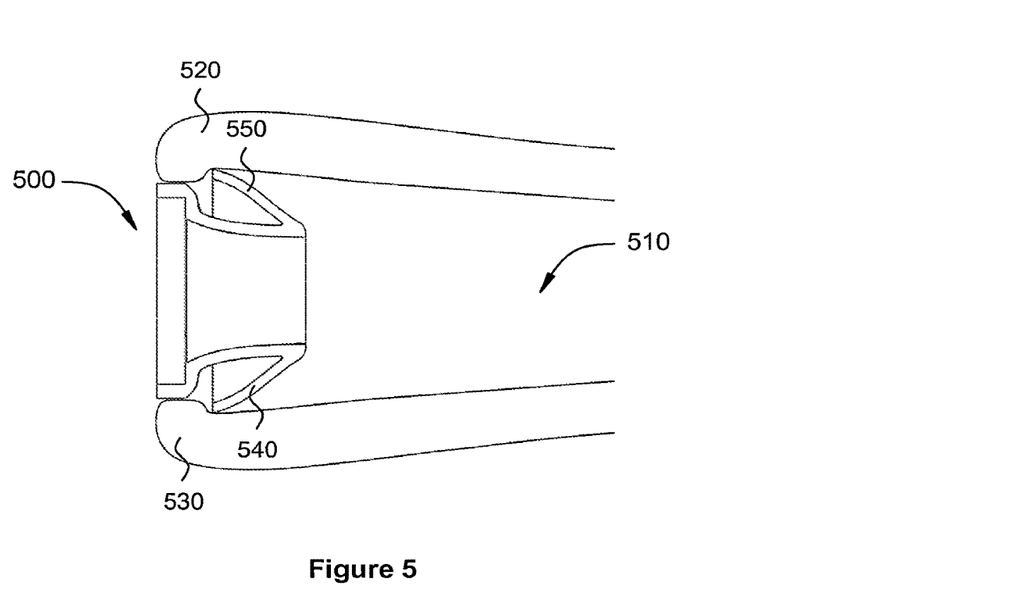
FIG. 5 illustrates the nasal pillow of FIG. 2 as inserted into the naris of a patient, according to one embodiment of the present invention.

FIG. 5 illustrates a nasal pillow 500 inserted into the naris 510 of a patient, according to one embodiment of the present invention. As shown, when the nasal pillow 500 is inserted, the nasal pillow 500 engages with, or latches onto, points along the inside wall of the naris 510 that are outside the area circumscribed by the entrance of the naris, such as a first point along the naris 510 near the tip 520 of the nose and a second point along the naris 510 near the base of the nose 530. In so doing, the nasal pillow 500 advantageously latches and secures the interface assembly of the entrainment device (not explicitly shown) within the nose without the need for head straps.

Insertion of the nasal pillow 500 into the nose provides improved anchoring by reducing the tendency of the entrainment device to roll out of or slide off of the nose. In some embodiments, the bottom edge 540 of the outer wall of the nasal pillow 500 may be positioned such that the bottom edge 540 may latch into place behind undercuts present just past the anterior naris 530. Likewise, the top edge 550 of the outer wall of the nasal pillow 500 may be positioned such that the top edge 550 may latch into place behind undercuts present just past the tip 520 of the nose. When inserted, the nasal pillow 500 forms a substantially airtight seal against the interior walls of the nostril.

Figure 6A:
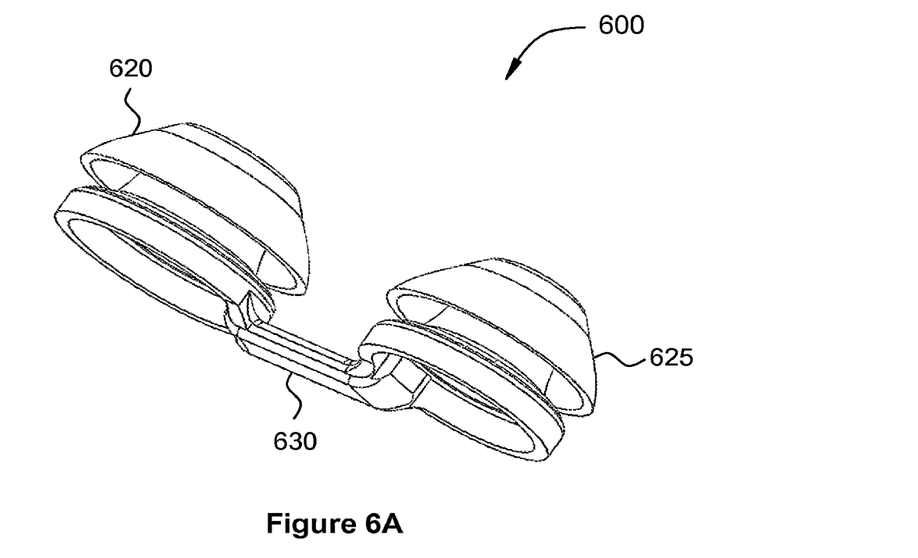
FIGS. 6A-6B illustrates an oblique view and a side view, respectively, of a nasal pillow apparatus, according to one embodiment of the present invention.
Figure 6B:
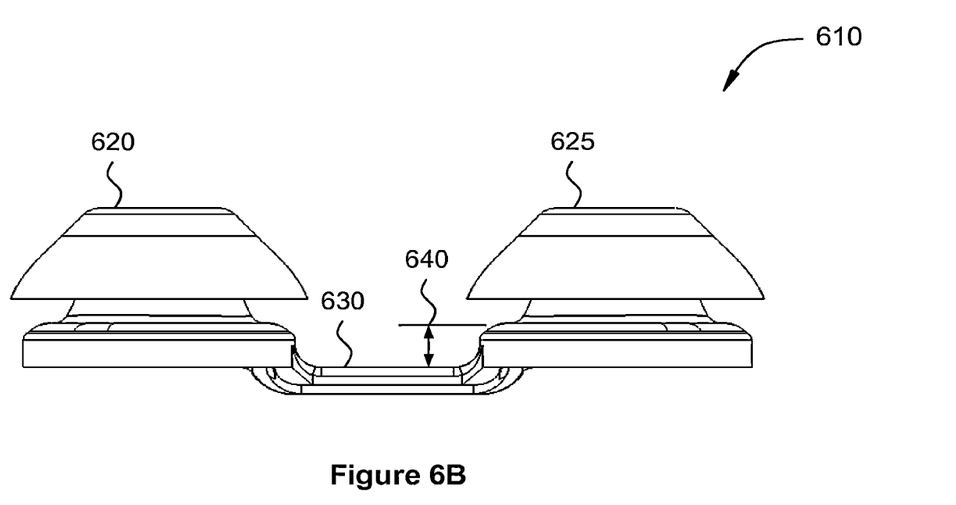

FIGS. 6A-6B illustrate an oblique view and a side view, respectively, of a nasal pillow apparatus 600, according to one embodiment of the present invention. As shown, the nasal pillow apparatus 600 includes, without limitation, a pair of nasal pillows, including a first nasal pillow 620 and a second nasal pillow 625, and a connecting bar 630. As described herein, the nasal pillows 620 and 625 are retained within the nares during breathing, reducing the likelihood that the entrainment device becomes dislodged during use. Even so, the nasal pillows 620 and 625 may, in some embodiments, may be connected via a connecting bar 630 to achieve greater stability.

The connecting bar 630 is typically made of a flexible material in order to allow the nasal pillows 620 and 625 to be freely positioned within into the nares. That is, the connecting bar 630 allows the nasal pillows 620 and 625 to gimbal, or swivel, relative to each other in order to accommodate varying naris angles from patient to patient. As shown, the connecting bar 630 is disposed below the bottom of the nasal pillows 620 and 625 by a distance 640. The distance 640 allows for full insertion of the nasal pillows 620 and 625 into the nose. The connecting bar 630 being disposed below the bottom surface of the nasal pillows 620 and 625 allows clearance for the columella of the nose. For example, if, the connecting bar 630 was level with the bottom surface of the nasal pillows 620 and 625, then the connecting bar 630 would interfere with the columella of the nose, the insertion level of the nasal pillows 620 and 625 within the nares would be limited, and the anchoring of the nasal pillows 620 and 625 within the nares would thereby be compromised.

It will be appreciated that the embodiments shown and described herein are illustrative and that variations and modifications are possible. In one example, the nares of the patient are generally described herein as elliptical in shape. However, the nares of a particular individual could include more complicated geometries. Accordingly, more complex nasal pillow designs, applicable to more complicated naris geometries, are within the scope of the present disclosure.

The conforming traits of the nasal pillow design described herein accommodate a broad range of naris shapes as evident in the broad range in elliptical ratios to which present pillows can conform.

In sum, a nasal pillow is disclosed for delivering a breathable gas, such as oxygen-enriched air, to a patient using a positive pressure breathing support device. The nasal pillows include geometrical features to allow for insertion of the nasal pillows deeply into the nares and provide sealing for positive pressure delivery without needing significant compression between the nasal pillows and the nasal openings. The design of the nasal pillows provides anchoring of an air entrainment device to the nostrils of a patient without the need for retaining head straps. Further, a connecting bar between a pair of nasal pillows is disposed below the bottom surface of the nasal pillows, providing room for the septum.

At least one advantage of the disclosed techniques is that the size of the air entrainment device and the nasal pillows is reduced relative to prior approaches. As a result, the breathing support device is less cumbersome for the patient to use. Another advantage of the disclosed approach is that less compression is needed to form a seal against the nasal opening and to retain the nasal pillows within the nares of the patient, leading to improved patient comfort and a reduced likelihood of the nasal pillows becoming dislodged during use.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

While the preceding is directed to embodiments of the present disclosure, other and further embodiments of the disclosure may be devised without departing from the basic scope thereof, and the scope thereof is determined by the claims that follow.

What is claimed is:

1. A nasal interface comprising:
   a first nasal pillow configured to secure at least partially within a first nostril of a user, the first nasal pillow comprising:
      a first end and a second end opposite the first end, the first end configured to be positioned farther inside the first nostril than the second end when the nasal interface is in use;
      an inner wall extending from the first end towards the second end, the inner wall forming an interior cavity configured to guide gas flow into the first nostril when the nasal interface is in use, the inner wall having a shape that converges towards the first end of the first nasal pillow;
      an outer wall connected to the inner wall at the first end of the first nasal pillow and extending radially outward from and around the inner wall thereby forming a gap between the inner and outer walls of the first nasal pillow, the outer wall configured to at least partially deform when inserted into the first nostril and further configured to anchor the first nasal pillow to the first nostril when the nasal interface is in use; and
      an interconnection at the second end of the first nasal pillow and configured to be connected to a first air entrainment device or a tube connected to the first air entrainment device; and
   a second nasal pillow configured to secure at least partially within a second nostril of the user, the second nasal pillow comprising:
      a first end and a second end opposite the first end of the second nasal pillow, the first end of the second nasal pillow configured to be positioned farther inside the second nostril than the second end of the second nasal pillow when the nasal interface is in use;
      an inner wall extending from the first end of the second nasal pillow towards the second end of the second nasal pillow, the inner wall of the second nasal pillow forming an interior cavity configured to guide gas flow into the second nostril when the nasal interface is in use, the inner wall of the second nasal pillow having a shape that converges towards the first end of the second nasal pillow;
      an outer wall connected to the inner wall of the second nasal pillow at the first end of the second nasal pillow and extending radially outward from and around the inner wall of the second nasal pillow thereby forming a gap between the inner and outer walls of the second nasal pillow, the outer wall of the second nasal pillow configured to at least partially deform when inserted into the second nostril and further configured to anchor the second nasal pillow to the second nostril when the nasal interface is in use; and
      an interconnection at the second end of the second nasal pillow and configured to be connected to a second air entrainment device or a tube connected to the second air entrainment device; and
   a connecting bar extending between and connecting the first and second nasal pillows to one another, the connecting bar made of a flexible material configured to allow the first and second nasal pillows to gimbal relative to one another, the connecting bar comprising:
      a first curved portion connected to the interconnection of the first nasal pillow at the second end of the first nasal pillow;
      a second curved portion connected to the interconnection of the second nasal pillow at the second end of the second nasal pillow; and
      a substantially straight portion connected to and extending between the first and second curved portions of the connecting bar, the substantially straight portion comprising a top surface configured to face toward a columella of the user when the nasal pillow interface is in use and a bottom surface configured to face away from the columella of the user when the nasal pillow interface is in use, wherein the bottom surface is spaced from a plane of each of the second ends of the first and second nasal pillows.

2. The nasal interface of claim 1, wherein:
   the outer wall of the first nasal pillow is configured to form a seal within the first nostril of the user; and
   the outer wall of the second nasal pillow is configured to form a seal within the second nostril of the user.

3. The nasal interface of claim 1, wherein the nasal interface is configured to secure to the first and second nostrils of the user without the use of a head strap.

4. The nasal interface of claim 1, wherein:
   a ratio of a minor axis of a cross section of the outer wall of the first nasal pillow to a major axis of the cross section of the outer wall of the first nasal pillow is between 0.8 to 1 prior to insertion into the first nostril of the user; and
   a ratio of a minor axis of a cross section of the outer wall of the second nasal pillow to a major axis of the cross section of the outer wall of the second nasal pillow is between of 0.8 to 1 prior to insertion into the second nostril of the user.

5. A system comprising the nasal interface of claim 1 and further comprising said first and second air entrainment devices, wherein said first and second air entrainment devices are configured to entrain ambient air with delivered oxygen, and wherein the interior cavities formed by the inner walls of the first and second nasal pillows are configured to guide said entrained ambient air and delivered oxygen into the first and second nostrils of the user.

6. The system of claim 5, wherein the interconnection of the first nasal pillow is overmolded over a portion of the first air entrainment device and wherein the interconnection of the second nasal pillow is overmolded over a portion of the second air entrainment device.

7. The system of claim 5, wherein the interconnection at the second end of the first nasal pillow is adhesively connected to a tube of the first air entrainment device and wherein the interconnection at the second end of the second nasal pillow is adhesively connected to a tube of the second air entrainment device.

8. A nasal interface comprising:
a first nasal pillow configured to secure at least partially within a first nostril of a user, the first nasal pillow comprising:
a first end and a second end opposite the first end, the first end configured to be positioned farther inside the first nostril than the second end when the nasal interface is in use;
an inner wall extending from the first end towards the second end, the inner wall forming an interior cavity configured to guide gas flow into the first nostril when the nasal interface is in use; and
an outer wall connected to the inner wall at the first end of the first nasal pillow and extending radially outward from and around the inner wall thereby forming a gap between the inner and outer walls of the first nasal pillow, the outer wall configured to at least partially deform when inserted into the first nostril and further configured to anchor the first nasal pillow to the first nostril when the nasal interface is in use; and
a second nasal pillow configured to secure at least partially within a second nostril of the user, the second nasal pillow comprising:
a first end and a second end opposite the first end of the second nasal pillow, the first end of the second nasal pillow configured to be positioned farther inside the second nostril than the second end of the second nasal pillow when the nasal interface is in use;
an inner wall extending from the first end of the second nasal pillow towards the second end of the second nasal pillow, the inner wall of the second nasal pillow forming an interior cavity configured to guide gas flow into the second nostril when the nasal interface is in use; and
an outer wall connected to the inner wall of the second nasal pillow at the first end of the second nasal pillow and extending radially outward from and around the inner wall of the second nasal pillow thereby forming a gap between the inner and outer walls of the second nasal pillow, the outer wall of the second nasal pillow configured to at least partially deform when inserted into the second nostril and further configured to anchor the second nasal pillow to the second nostril when the nasal interface is in use; and a connecting bar extending between and connecting the first and second nasal pillows to one another, the connecting bar made of a flexible material configured to allow the first and second nasal pillows to gimbal relative to one another, the connecting bar comprising:
a first curved portion connected to the second end of the first nasal pillow;
a second curved portion connected to the second end of the second nasal pillow; and
a substantially straight portion connected to and extending between the first and second curved portions of the connecting bar, the substantially straight portion comprising a top surface configured to face toward a columella of the user when the nasal pillow interface is in use and a bottom surface configured to face away from the columella of the user when the nasal pillow interface is in use, wherein the bottom surface is spaced from a plane of each of the second ends of the first and second nasal pillows.

9. The nasal interface of claim 8, wherein:
the outer wall of the first nasal pillow is configured to form a seal within the first nostril of the user; and
the outer wall of the second nasal pillow is configured to form a seal within the second nostril of the user.

10. The nasal interface of claim 8, wherein the inner wall of the first nasal pillow has a shape that converges towards the first end of the first nasal pillow, and wherein the inner wall of the second nasal pillow has a shape that converges towards the first end of the second nasal pillow.

11. The nasal interface of claim 8, wherein the nasal interface is configured to secure to the first and second nostrils of the user without the use of a head strap.

12. A system comprising the nasal interface of claim 8 and further comprising a first air entrainment device connected to the second end of the first nasal pillow and a second air entrainment device connected to the second end of the second nasal pillow, wherein the first and second air entrainment devices are configured to entrain ambient air with delivered oxygen, and wherein the interior cavities formed by the inner walls of the first and second nasal pillows are configured to guide said entrained ambient air and delivered oxygen into the first and second nostrils of the user.

13. The system of claim 12, wherein the first nasal pillow is integrally formed with a portion of the first air entrainment device and wherein the second nasal pillow is integrally formed with a portion of the second air entrainment device.

14. The system of claim 12, wherein each of the first and second ends of the first and second nasal pillows is connected to delivery tube.

15. A nasal interface comprising:
a first nasal pillow configured to secure at least partially within a first nostril of a user;
a second nasal pillow configured to secure at least partially within a second nostril of the user;
wherein each of the first and second nasal pillows comprises:
a first end and a second end opposite the first end;
an inner wall forming an interior cavity;
an outer wall connected to the inner wall at the first end and extending radially outward from and around the inner wall thereby forming a gap between the inner and outer walls, the outer wall configured to secure within one of the first and second nostrils of the user;
the nasal interface further comprising a connecting bar extending between and connecting the first and second nasal pillows to one another, the connecting bar comprising:

a first curved portion connected to the first nasal pillow at the second end of the first nasal pillow;

a second curved portion connected to the second nasal pillow at the second end of the second nasal pillow; and a substantially straight portion connected to and extending between the first and second curved portions of the connecting bar, the substantially straight portion comprising a top surface configured to face toward a columella of the user when the nasal pillow interface is in use and a bottom surface configured to face away from the columella of the user when the nasal pillow interface is in use, wherein the bottom surface is spaced from a plane of each of the second ends of the first and second nasal pillows.

16. The nasal interface of claim 15, wherein the outer wall is configured to form a seal against interior walls of the one of the first and second nostrils of the user.

17. A system comprising the nasal interface of claim 15 and further comprising a first air entrainment device connected at the second end of the first nasal pillow and a second air entrainment device connected at the second end of the second nasal pillow, wherein the interior cavities formed by the inner walls of the first and second nasal pillows are configured to guide entrained ambient air and delivered oxygen into the first and second nostrils of the user.

18. The nasal interface of claim 15, wherein the nasal interface is configured to secure to the first and second nostrils of the user without the use of a head strap.

19. The nasal interface of claim 15, wherein the inner wall has a shape that converges towards the first end.

20. The nasal interface of claim 15, wherein the connecting bar is made of a flexible material configured to allow the first and second nasal pillows to gimbal relative to one another.

* * * * *